US011249154B2

(12) United States Patent
Mori et al.

(10) Patent No.: US 11,249,154 B2
(45) Date of Patent: Feb. 15, 2022

(54) MAGNETIC RESONANCE IMAGING APPARATUS

(71) Applicant: Canon Medical Systems Corporation, Otawara (JP)

(72) Inventors: Takaya Mori, Nasushiobara (JP); Keiichiro Ishi, Tsukuba (JP); Yoshimori Kassai, Nasushiobara (JP); Sho Tanaka, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 533 days.

(21) Appl. No.: 16/191,927

(22) Filed: Nov. 15, 2018

(65) Prior Publication Data

US 2019/0146044 A1 May 16, 2019

(30) Foreign Application Priority Data

Nov. 16, 2017 (JP) .............................. JP2017-220682

(51) Int. Cl.
*G01R 33/24* (2006.01)
*G01R 33/385* (2006.01)
(Continued)

(52) U.S. Cl.
CPC ............ *G01R 33/246* (2013.01); *A61B 5/055* (2013.01); *G01R 33/385* (2013.01); *G01R 33/4835* (2013.01); *G01R 33/543* (2013.01); *G01R 33/5659* (2013.01); *G01R 33/583* (2013.01); *G06T 7/0012* (2013.01); *G06T 2207/10088* (2013.01); *G06T 2207/30048* (2013.01)

(58) Field of Classification Search
CPC .............. G01R 33/246; G01R 33/5659; G01R 33/543; G01R 33/4835; G01R 33/583; G01R 33/385; G01R 33/565; G01R 33/56563; A61B 5/055; G06T 7/0012; G06T 2207/10088; G06T 2207/30048
See application file for complete search history.

(56) References Cited

U.S. PATENT DOCUMENTS

2012/0161766 A1 6/2012 Harvey et al.
2013/0144156 A1* 6/2013 Boulant ............. G01R 33/5612
600/410
(Continued)

FOREIGN PATENT DOCUMENTS

JP 2011-131045 A 7/2011

OTHER PUBLICATIONS

Japanese Office Action dated Oct. 12, 2021, issued in Japanese Patent Application No. 2017-220682.

*Primary Examiner* — Amelie R Davis
(74) *Attorney, Agent, or Firm* — Oblon, McClelland, Maier & Neustadt, L.L.P.

(57) ABSTRACT

According to one embodiment, a magnetic resonance imaging apparatus includes processing circuitry. The processing circuitry calculates power of a first RF magnetic field required for excitation at a first flip angle in a first target slice, acquires information on inhomogeneity of a transmission RF magnetic field for a cross section crossing the first target slice, and calculate power of a second RF magnetic field required for excitation at a second flip angle in a second target slice different from the first target slice for the cross section by using the information and the first RF magnetic field power.

12 Claims, 6 Drawing Sheets

(51) Int. Cl.
*A61B 5/055* (2006.01)
*G06T 7/00* (2017.01)
*G01R 33/565* (2006.01)
*G01R 33/54* (2006.01)
*G01R 33/483* (2006.01)
*G01R 33/58* (2006.01)

(56) References Cited

U.S. PATENT DOCUMENTS

2016/0282438 A1 9/2016 Sun et al.
2017/0242085 A1* 8/2017 Koehler ............. G01R 33/5659

* cited by examiner

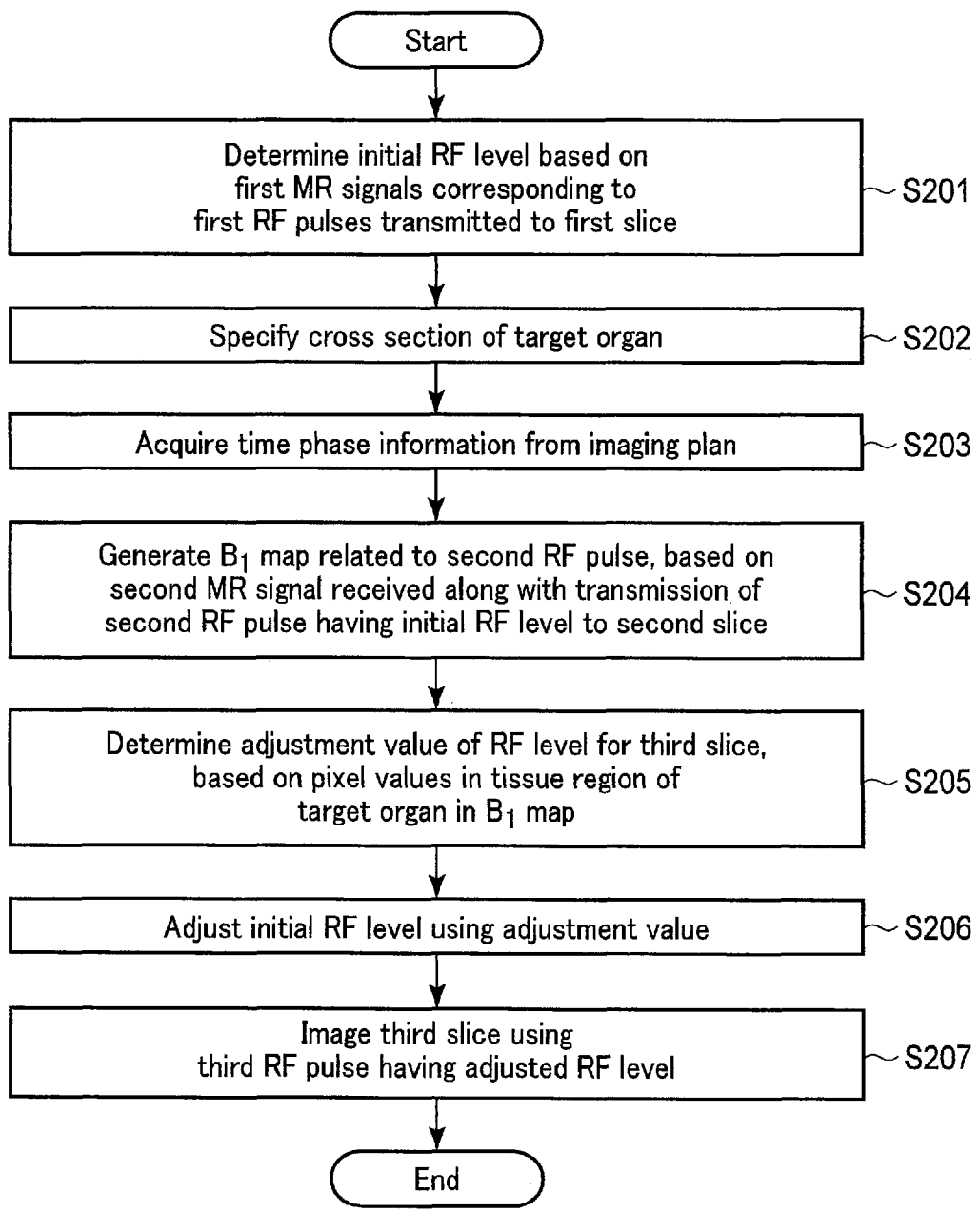
F I G. 2

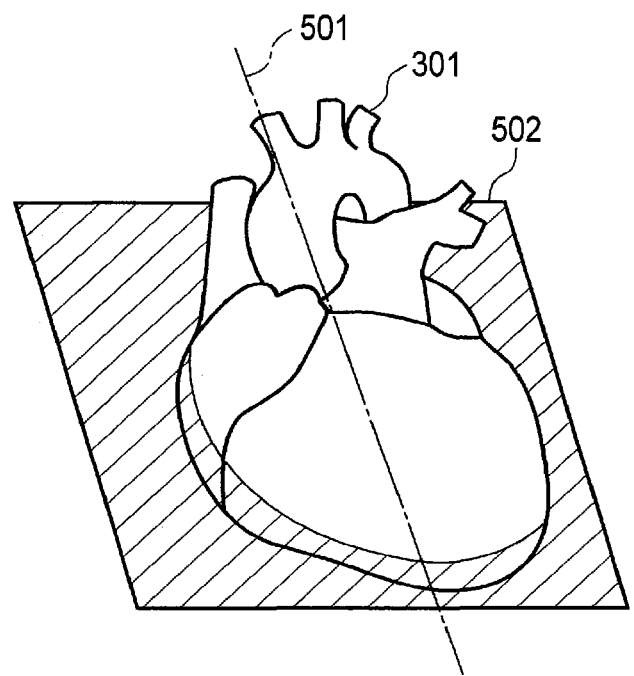
F I G. 5
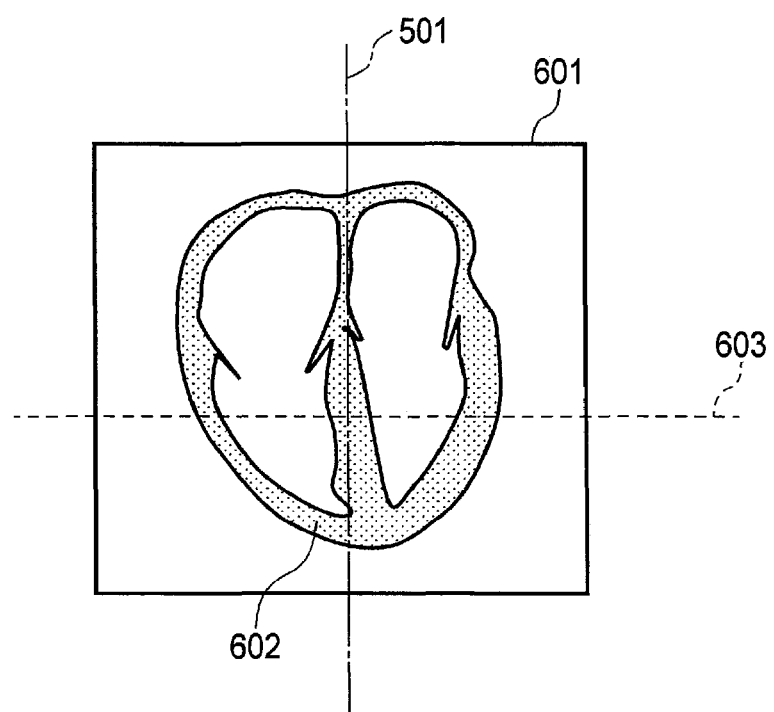
F I G. 6

| Pixel value of $B_1$ map | Adjustment value of RF level(dB) |
|---|---|
| ⋮ | ⋮ |
| 70 | R_1 |
| 75 | R_2 |
| 80 | R_3 |
| ⋮ | ⋮ |

MAGNETIC RESONANCE IMAGING APPARATUS

CROSS-REFERENCE TO RELATED APPLICATIONS

This application is based upon and claims the benefit of priority from Japanese Patent Application No. 2017-220682, filed Nov. 16, 2017, the entire contents of which are incorporated herein by reference.

FIELD

Embodiments described herein relate generally to a magnetic resonance imaging apparatus.

BACKGROUND

Magnetic Resonance Imaging (MRI) apparatuses require a determination of the transmit strength (referred to as "RF level") of Radio Frequency (RF) signals before performing a main scan. When determining the RF level, the MRI apparatuses estimate the RF level based on the relationship between the transmit strength of RF signals and the receive strength of magnetic resonance (MR) signals for a broad imaging region such as a chest or an abdomen. For example, when imaging the heart, the MRI apparatuses estimate the RF level based on a chest that includes the heart.

However, the estimated RF level may not be set at a level suitable for a target organ. Thus, it is required to calculate an RF magnetic field power suitable for imaging on the target organ.

BRIEF DESCRIPTION OF THE DRAWINGS

FIG. 2 is a flowchart of an operation according to the embodiment.

FIG. 5 illustrates a cross section position including a cardiac axis of the heart, according to the embodiment.

FIG. 6 illustrates an image of the cross section including the cardiac axis of the heart, according to the embodiment.

DETAILED DESCRIPTION

According to one embodiment, a magnetic resonance imaging apparatus includes processing circuitry. The processing circuitry calculates power of a first RF magnetic field required for excitation at a first flip angle in a first target slice, acquires information on inhomogeneity of a transmission RF magnetic field for a cross section crossing the first target slice and calculate power of a second RF magnetic field required for excitation at a second flip angle in a second target slice different from the first target slice for the cross section by using the information and the first RF magnetic field power.

Hereinafter, the present embodiments of a magnetic resonance imaging apparatus will be explained in detail with reference to the accompanying drawings.

Embodiment

Figure 1:
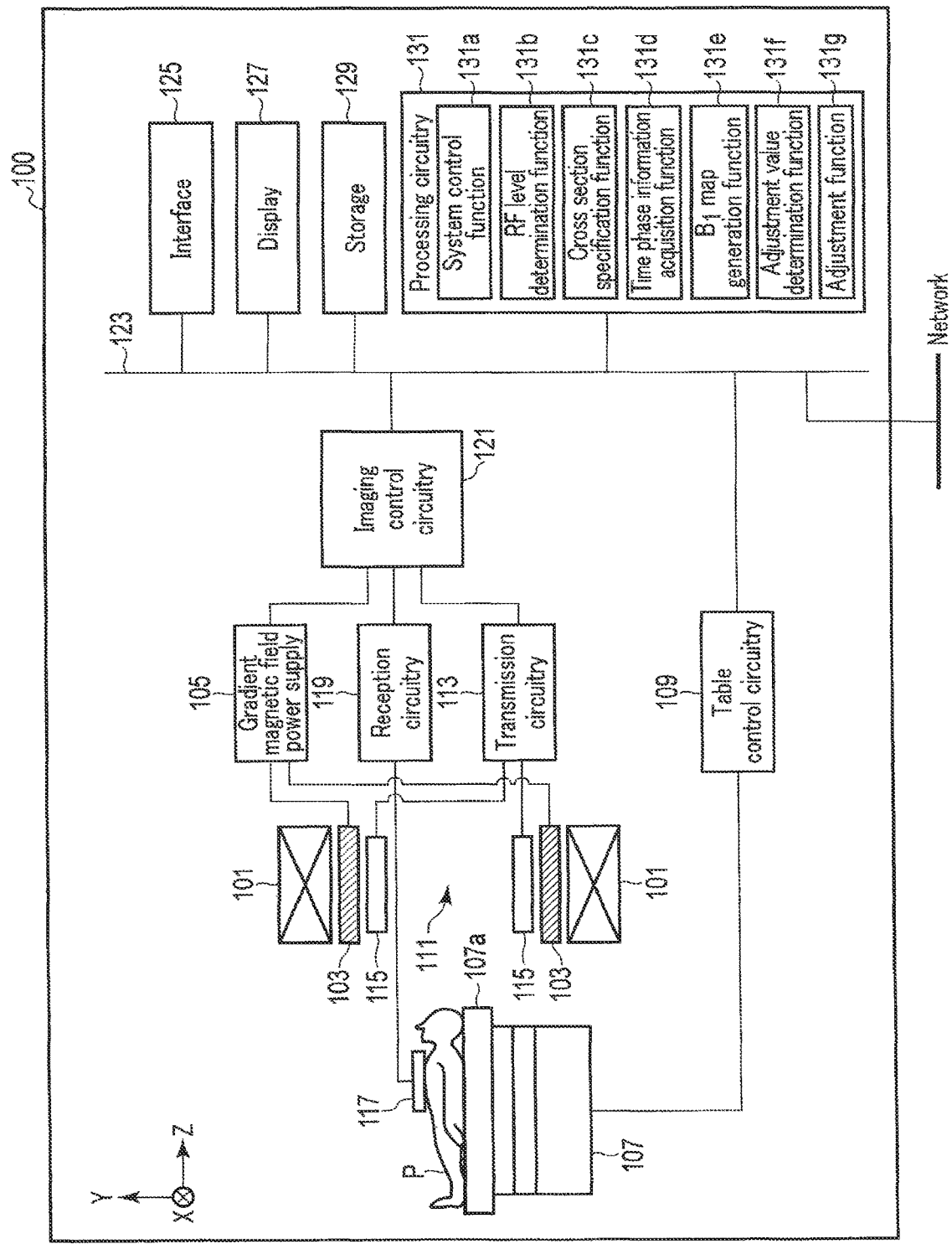
FIG. 1 is a block diagram illustrating the configuration of an MRI apparatus according to an embodiment.

FIG. 1 illustrates an MRI apparatus 100 according to an embodiment. The MRI apparatus 100 includes a static field magnet 101, a gradient coil 103, a gradient magnetic field power supply 105, a table 107, table control circuitry 109, a transmission circuitry 113, a transmission coil 115, a reception coil 117, a reception circuitry 119, imaging control circuitry 121, a bus 123, an interface 125, a display 127, a storage 129, and processing circuitry 131. The MRI apparatus 100 may have a hollow cylindrical-shaped shim coil provided between the static field magnet 101 and the gradient coil 103.

The static field magnet 101 is, for example, a magnet formed in a hollow and essentially cylindrical shape. The static field magnet 101 generates a homogeneous static magnetic field in a bore 111 which is an inner space into which a subject P is inserted. For example, a superconductive magnet, etc. may be used for the static field magnet 101.

The gradient coil 103 is a coil formed in a hollow cylindrical shape. The gradient coil 103 is arranged inside of the static field magnet 101. The gradient coil 103 is formed by combining three coils respectively corresponding to the X-, Y-, and Z-axes which are orthogonal to each other. The Z-axis direction is defined as the same as the orientation of the static magnetic field. In addition, the Y-axis direction is a vertical direction, and the X-axis direction is a direction perpendicular to each of the Z-axis and the Y-axis. The gradient coil 103 generates a gradient field to be superimposed onto the static magnetic field. Specifically, these three coils in the gradient coil 103 are separately supplied with a current from the gradient magnetic field power supply 105, and respectively generate gradient fields in which a magnetic field intensity changes along each of the X-, Y-, and Z-axes.

The gradient fields along each of the X-, Y-, and Z-axes generated by the gradient coil 103 respectively form, for example, a frequency encode gradient field (readout gradient field), a phase encode gradient field, and a slice selective gradient field. The frequency encode gradient field is used to change a frequency of an MR signal in accordance with a spatial position. The phase encode gradient field is used to change the phase of magnetic resonance (MR) signals in accordance with a spatial position. The slice selective gradient field is used to determine an imaging cross section.

The gradient magnetic field power supply 105 is a power supply apparatus that supplies a current to the gradient coil 103 by the control of the imaging control circuitry 121.

The table 107 is an apparatus having the table top 107a on which a subject P is placed. The table 107 inserts the table top 107a, on which the subject P is placed, into the bore 111 under the control of the table control circuitry 109. The table 107 is installed in an examination room, where the MRI apparatus 100 is installed, in such a manner that the longitudinal axis of the table 107 is parallel to the central axis of the static field magnet 101.

The table control circuitry 109 is circuitry that controls the table 107 in response to an operator's instruction via the interface 125 to move the table top 107a in a longitudinal direction and a vertical direction.

The transmission circuitry 113 supplies a high frequency pulse corresponding to a Larmor frequency to the transmission coil 115 by the control of the imaging control circuitry 121.

The transmission coil 115 is an RF coil disposed inside of the gradient coil 103. The transmission coil 115 receives an RF signal from the transmission circuitry 113, and generates a transmission RF wave (RF pulse) which corresponds to a high frequency magnetic field. The transmission coil is, for example, a whole body (WB) coil. The WB coil may be used as a transmission/reception coil.

The reception coil 117 is an RF coil disposed inside of the gradient coil 103. The reception coil 117 receives an MR signal emitted from the subject P, caused by the high frequency magnetic field. The reception coil 117 outputs the received MR signal to the reception circuitry 119. The reception coil 117 is, for example, a coil array having one or more coil elements, typically having a plurality of coil elements. In FIG. 1, the transmission coil 115 and the reception coil 117 are illustrated as separate RF coils; however, the transmission coil 115 and the reception coil 117 may be implemented as an integrated transmission/reception coil. The transmission/reception coil is, for example, a local transmission/reception RF coil, such as a head coil, to serve as an imaging target in the subject P.

The reception circuitry 119 generates, under the control of the imaging control circuitry 121, a digital MR signal, which is digitized complex number data, based on the MR signal that is output from the receive coil 117. Specifically, the reception circuitry 119 performs various types of signal processing to the MR signal output from the reception coil 117, and then performs analog-to-digital (A/D) conversion to the signal subjected to the signal processing. The reception circuitry 119 executes sampling to the A/D converted data to generate the digital MR signal (MR data). The reception circuitry 119 outputs the generated MR data to the imaging control circuitry 121.

The imaging control circuitry 121 controls the gradient magnetic field power supply 105, the transmission circuitry 113, and the reception circuitry 119, etc. in accordance with an imaging protocol output from the processing circuitry 131, and performs imaging on the subject P. The imaging protocol has different pulse sequences in accordance with a type of examination. The imaging protocol includes a magnitude of a current supplied by the gradient magnetic field power supply 105 to the gradient coil 103, timing of supplying a current by the gradient magnetic field power supply 105 to the gradient coil 103, a magnitude of an RF signal supplied by the transmission circuitry 113 to the transmission coil 115, timing of supplying an RF signal by the transmission circuitry 113 to the transmission coil 115, timing of receiving an MR signal by the reception coil 117, etc. The term "imaging" may refer to "performing an imaging scan".

The bus 123 is a transmission path through which data is transmitted between the interface 125, the display 127, the storage 129, and the processing circuitry 131. The bus 123 may be connected to various biosignal measuring instruments, external storage devices, various modalities, etc. via a network, etc. For example, a non-illustrated electrocardiograph is connected to the bus, as a physiological signal measuring device.

The interface 125 has circuitry for receiving various types of instructions and information input from an operator. The interface 125 is circuitry for a pointing device, such as a mouse, or for an input device, such as a keyboard, etc. The interface 125 is not limited to circuitry for physical operation members such as a mouse and a keyboard. For example, the interface 125 may include electric signal processing circuitry that receives an electric signal corresponding to an input operation through an external input device provided separately from the MRI apparatus 100 and outputs the received electric signal to various types of circuitry.

The display 127 displays various types of information regarding imaging and image processing, various types of MR images generated by an image generation function, under the control of a system control function 131a in the processing circuitry 131 described later. The display 127 is, for example, a CRT display, a liquid crystal display, an organic EL display, an LED display, a plasma display, any other display known in this technical field, or a monitor, etc.

The storage 129 stores MR data arranged in k-space by the image generation function, and image data generated by the image generation function, etc. The storage 129 stores various types of imaging protocols, and imaging conditions including imaging parameters that define the imaging protocols, etc. The storage 129 stores programs corresponding to the various types of functions executed by the processing circuitry 131. The storage 129 is, for example, a RAM (Random Access Memory), a semiconductor memory element such as a flash memory, a hard disk drive, a solid state drive, an optical disk, etc. The storage 129 may be a drive, etc. configured to read and write various types of information with respect to a portable storage medium such as a CD-ROM drive, a DVD drive, or a flash memory, etc.

The processing circuitry 131 includes a non-illustrated processor, and a non-illustrated memory such as a ROM (Read-Only Memory) or a RAM, etc. as hardware resources, to integrally control the MRI apparatus 100. The processing circuitry 131 includes a system control function 131a, an RF level determination function 131b, a cross section specification function 131c, a time phase information acquisition function 131d, a $B_1$ map generation function 131e, an adjustment value determination function 131f, and an adjustment function 131g. The various functions, which are performed by the RF level determination function 131b, the cross section specification function 131c, the time phase information acquisition function 131d, the $B_1$ map generation function 131e, the adjustment value determination function 131f, and the adjustment function 131g, are stored in the storage 129, each in a form of a computer-executable program. The processing circuitry 131 is a processor which reads a program corresponding to each function from the storage 129 and executes the program to activate the function corresponding to the program. In other words, the processing circuitry 131 which has read each program can activate each function shown in the processing circuitry 131 of FIG. 1.

FIG. 1 illustrates that the aforementioned functions are implemented by a single processing circuitry 131; however, the processing circuitry 131 may include a plurality of independent processors, and the functions may be implemented by the processors executing respective programs. In other words, there may be a case where each of the aforementioned functions may be configured as a program, and a single processing circuitry executes each program, or a case where each of the functions may be implemented in independent program-execution circuitry specific to respective functions. The term "processor" used in the above description refers to, for example, a CPU (Central Processing Unit), a GPU (Graphics Processing Unit), or circuitry such as an ASIC (Application Specific Integrated Circuit), a programmable logic device (for example, an SPLD (Simple Programmable Logic Device), a CPLD (Complex Programmable Logic Device), or an FPGA (Field Programmable Gate Array)).

The processor reads and executes a program stored in the storage 129 to activate the corresponding function. A program may be directly integrated into the circuitry of the processor, instead of storing the program on the storage 129. In this case, the function is activated by reading and executing the program integrated into the circuitry. The table control circuitry 109, the transmission circuitry 113, the reception circuitry 119, and the imaging control circuitry 121, etc. are also similarly configured as electronic circuitry such as the above processor, etc.

The system control function 131a is a function of controlling the MRI apparatus 100. Specifically, via the system control function 131a, the processing circuitry 131 reads a system control program stored in the storage 129, deploys the program on a memory, and controls the respective circuitry of the MRI apparatus 100 in accordance with the deployed system control program. For example, via the system control function 131a, the processing circuitry 131 reads an imaging protocol from the storage 129 based on imaging conditions input by an operator through the interface 125. The processing circuitry 131, via the system control function 131a, transmits the imaging protocol to the imaging control circuitry 121 to control imaging on the subject P. The processing circuitry 131 may generate via the system control function 131a the imaging protocol based on the RF level adjusted by the adjustment function 131g.

The RF level determination function 131b is a function of determining an initial value of the RF level (initial RF level). The RF level is, for example, a level indicating an electric power to rotate the spin of an atom by approximately 90° in the subject P. Namely, the RF level corresponds to power of an RF pulse and represents an amplitude of an RF pulse. In other words, via the RF level determination function 131b, the processing circuitry 131 determines an amplitude of an RF pulse based on a high-frequency magnetic field transmitted or received relative to the subject P through an RF coil. The initial RF level is, for example, an RF level optimized for the entire chest region or abdomen region that includes a target organ, i.e., an FOV (Field Of View) that includes the target organ.

Specifically, the processing circuitry 131, via the RF level determination function 131b, determines an RF level indicating the level of power supplied to the RF coil based on a plurality of first MR signals corresponding to a plurality of first RF pulses transmitted to a first slice of the target organ. The power supplied to the RF coil (referred to as "RF magnetic field power") has a correlation with the receive strength of MR signals. The receive strength of MR signals is, for example, a signal value of MR data (projection data) acquired without performing phase encoding. The processing circuitry 131, via the RF level determination function 131b, determines, for example, the transmit power relative to the transmit strength of RF signals corresponding to the maximum value of the receive strength of MR signals as the initial RF level.

The first slice is, for example, a slice that includes the entire chest region or abdomen region that includes the target organ. The first RF pulses are, for example, RF pulses which correspond to different levels of the transmit strength of RF signals. If the target organ is the heart, the processing circuitry 131, via the RF level determination function 131b, determines the initial RF level by using a slice of the chest region that includes the heart. The initial RF level is determined at a pre-scan performed prior to the main scan. The first slice may be referred to as a "first target slice".

The processing circuitry 131, via the RF level determination function 131b, may calculate the power of the RF magnetic field required for excitation at a predetermined flip angle. Specifically, the processing circuitry 131, via the RF level determination function 131b, calculates the power of a first RF magnetic field required for excitation at a first flip angle in the first target slice.

The cross section specification function 131c is a function of specifying a cross section of the target organ. Specifically, the processing circuitry 131, via the cross section specification function 131c, specifies a second slice and a third slice by executing measurement for positioning of the target organ (locator imaging). The processing circuitry 131, via the cross section specification function 131c, may specify a cross section by the operator's instruction through the interface 125.

The second slice is, for example, a slice for a representative cross section in the target organ. The representative cross section is a cross section that includes a long axis of the target organ. If the target organ is the heart, the second slice is a slice for a cross section that includes the cardiac axis of the heart. The cardiac axis is, for example, a line connecting the cardiac base and the cardiac apex. The "cardiac axis of a heart" indicates the "long axis of a heart".

The third slice is, for example, a slice for a cross section crossing the representative cross section in the target organ. If the target organ is the heart, the third slice is a slice for a cross section that includes the cardiac axis of the heart. The third slice may be referred to as a "second target slice".

The second slice and the third slice correspond to a slice acquired by the two-dimensional multi-slice imaging, but are not limited thereto. For example, regarding the second slice and the third slice, "slice" may be a one-dimensional line profile deployed on a plane, or a cross section designated by using volume data of a 3D scan. Namely, the second slice and the third slice may be a slice in the general multi-slice, or a slice defined by other methods.

The time phase information acquisition function 131d is a function of acquiring information on a time phase from an imaging plan, etc. Specifically, the processing circuitry 131, via the time phase information acquisition function 131d, acquires information on a time phase at a timing of imaging the third slice relative to the target organ from the imaging plan indicating the process of imaging to be executed by the imaging control circuitry 121. Alternatively, since the timing of acquiring information on inhomogeneity of the transmission RF magnetic field is determined based on the imaging plan, the processing circuitry 131, via the time phase information acquisition function 131d, may acquire a cardiac time phase at a timing of acquiring information on inhomogeneity of the transmission RF magnetic field.

The information on time phase is, for example, information related to a time phase of at least one of a contraction time or an expansion time of the cardiac cycle of the heart. The information on time phase may be, for example, information related to a time phase of at least one of an exhalation phase or an inhalation phase in breathing of the subject P. The imaging plan includes, for example, information on "imaging in the contraction time", "imaging in the expansion time", and "cine imaging of the heart", when imaging the heart.

The $B_1$ map generation function 131e is a function of generating a $B_1$ map, which is the distribution of the receive strength of MR signals. Specifically, the processing circuitry 131, via the $B_1$ map generation function 131e, generates a $B_1$ map which represents the magnetic field strength distribution relative to a second RF pulse based on a second MR signal received along with transmission of the second RF pulse having the initial RF level to the second slice for the target organ.

In the case where the blood amount in the target organ varies in accordance with a heartbeat, or the shape of a target organ varies in accordance with breathing, it is desirable that the processing circuitry 131, via the $B_1$ map generation function 131e, generates a $B_1$ map in accordance with a heartbeat or breathing. The processing circuitry 131, via the $B_1$ map generation function 131e, generates a $B_1$ map corresponding to the time phase acquired by the time phase information acquisition function 131d.

Specifically, the processing circuitry 131, via the $B_1$ map generation function 131e, generates a $B_1$ map that corresponds to a time phase of at least one of the contraction time and the expansion time of the cardiac cycle of the heart if the target organ is the heart. In the contraction time, the blood in the heart is pushed out, and the strength of a signal from the blood represented in the $B_1$ map is lowered. Accordingly, the strength of a signal from the cardiac muscle becomes large, and the strength of a signal from the blood becomes small in the contraction time in comparison with the expansion time. The processing circuitry 131, via the $B_1$ map generation function 131e, generates a $B_1$ map corresponding to a time phase of at least one of the exhalation phase and the inhalation phase of breathing of the subject P if the target organ is, for example, the liver in the abdomen.

If a $B_1$ map is generated in accordance with a timing of each time phase, the magnetic resonance imaging apparatus 100 performs imaging by using an electrocardiograph waveform. In the case where the contraction time and the expansion time are distinguished from the electrocardiograph waveform, the magnetic resonance imaging apparatus 100 distinguishes the contraction time and the expansion time by, for example, using an R wave and a T wave of the electrocardiograph waveform. Specifically, the magnetic resonance imaging apparatus 100 identifies a time period from the peak of the R wave to the peak of the T wave in a cardiac cycle as the contraction time, and identifies a time period from the peak of the T wave to the peak of the R wave in the next cardiac cycle as the expansion time.

The magnetic resonance imaging apparatus 100 may identify the contraction time and the expansion time by using certain software to analyze the electrocardiograph waveform. Specifically, the magnetic resonance imaging apparatus 100 acquires a plurality of images which are different in cardiac time phase by changing a delay time from a synchronous signal (for example, R wave), and identifies the contraction time and the expansion time based on a signal value (for example, luminance value) analyzed based on the acquired images. The delay time may be manually set by an operator, or automatically set by certain software.

Via the $B_1$ map generation function 131e, it is desirable that the second MR signal is acquired via a method for suppressing an MR signal from the blood vessel of the target organ (for example, a Black Blood (BB) method). By using the BB method, the blood having a signal with a higher strength can be suppressed, and the operator can easily observe tissues in the target organ in the $B_1$ map. The imaging method when generating a $B_1$ map may, for example, be a combination of the BB method and a double angle method by using high-speed imaging such as a half Fourier single shot fast spin echo (FSE).

The processing circuitry 131, via the $B_1$ map generation function 131e, may generate or acquire information on inhomogeneity of the transmission RF magnetic field, instead of generating a $B_1$ map. Specifically, the processing circuitry 131, via the $B_1$ map generation function 131e, acquires information on inhomogeneity of the transmission RF magnetic field for a cross section crossing the first target slice. The information on inhomogeneity of the transmission RF magnetic field corresponds to, for example, luminance imbalance in an image which is represented by a $B_1$ map representing spatial inhomogeneity of the transmission RF magnetic field. Accordingly, the information on inhomogeneity of the transmission RF magnetic field may be, for example, a sensitivity map representing inhomogeneity of the reception coil sensitivity (coil sensitivity). The processing circuitry 131, via the $B_1$ map generation function 131e, may generate a sensitivity map. The information on inhomogeneity of the transmission RF magnetic field is not limited to two-dimensional information, but may also be three-dimensional information.

The adjustment value determination function 131f is a function of determining a value of increasing or decreasing the initial RF level (adjustment value) to obtain an optimized RF level for imaging of the target organ. The adjustment value is, for example, a decibel (dB) value.

Specifically, the processing circuitry 131, via the adjustment value determination function 131f, determines an adjustment value of an RF level for the third slice set relative to the target organ, based on a plurality of pixel values included in a tissue region of the target organ in the $B_1$ map generated by the $B_1$ map generation function 131e. For example, the processing circuitry 131, via the adjustment value determination function 131f, may determine an adjustment value based on an average value of the pixel values included in a partial region corresponding to the third slice in the $B_1$ map within the tissue region of the target organ in the $B_1$ map. The tissue region is a region in which a tissue is present in the target organ in the $B_1$ map. The pixel value is represented by a numerical value related to a ratio of the receive strength of an MR signal in relation to the transmit strength of an RF signal. For example, if the pixel value of a certain pixel on the $B_1$ map is 50, it indicates that the ratio of the receive strength of an MR signal in relation to the transmit strength of an RF signal is 50% in the tissue region corresponding to the certain pixel.

The processing circuitry 131, via the adjustment value determination function 131f, may determine an adjustment value by adopting, as a parameter, a pixel value of an average value to a given estimation equation, or determine an adjustment value by referring to a table (look up table) in which a pixel value or an average value is associated with an adjustment value.

The adjustment function 131g is a function of adjusting the initial RF level by using the adjustment value determined by the adjustment value determination function 131f. The processing circuitry 131, via the adjustment function 131g, outputs the adjusted RF level to the imaging control circuitry 121.

Via the processing of the adjustment value determination function 131f and the adjustment function 131g, the processing circuitry 131 may calculate the power of the second RF magnetic field by using the power of the first RF magnetic field. Specifically, the processing circuitry 131, via the adjustment value determination function 131f and the adjustment function 131g, calculates the power of the second RF magnetic field required for excitation at a second flip angle in a second target slice different from the first target slice for a cross section crossing the first target slice by using information on inhomogeneity of the transmission RF magnetic field and the first RF magnetic field power.

FIG. 2 illustrates the operation of the magnetic resonance imaging apparatus 100 having the aforementioned configuration. Next, the operation of adjusting an RF level suitable for imaging on the target organ will be described. In the example below, the target organ is the heart; however, the embodiment can be adopted to other organs.

First, the magnetic resonance imaging apparatus 100 initiates the operation of step S201, by selecting a program to adjust an RF level suitable for imaging on the target organ in response to the operator's instruction, and executing the program. In this case, the operator may set a slice position for determining the initial RF level via the interface 125.

(Step S201)

The processing circuitry 131, via the RF level determination function 131b, determines the initial RF level based on a plurality of first MR signals corresponding to a plurality of first RF pulses transmitted to the first slice.

Figure 3:
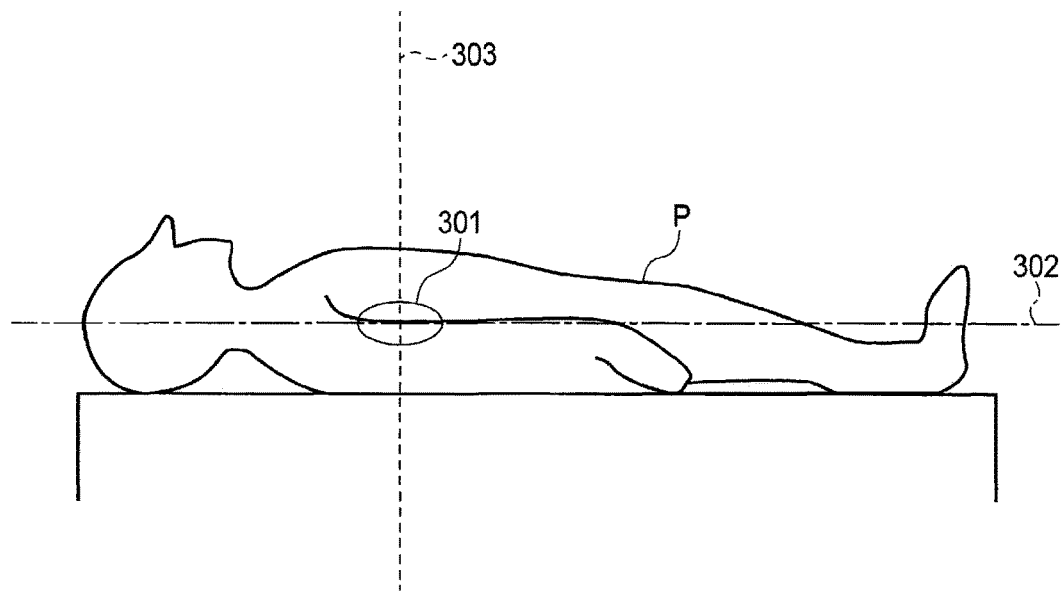
FIG. 3 illustrates a slice position of a chest that includes the heart, according to the embodiment.
Figure 4:
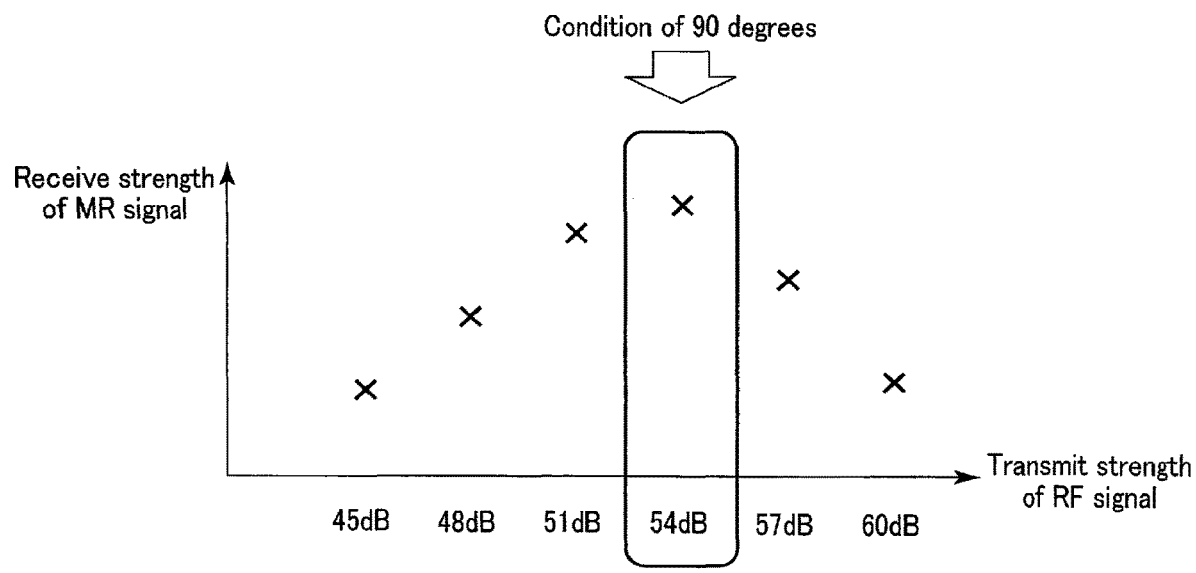
FIG. 4 illustrates the relationship between the transmit strength of an RF signal and the receive strength of an MR signal, according to the embodiment.

The method for determining the initial RF level will be described with reference to FIGS. 3 and 4. The processing circuitry 131, via the RF level determination function 131b, sets a slice position 303 crossing a body axis 302 of the subject P if a heart 301 is imaged as a target organ. The first slice in the slice position 303 includes the heart 301, and covers the entire circumference around the body axis of the subject P.

The processing circuitry 131, via the RF level determination function 131b, changes the transmit strength of RF signals step by step relative to the first slice, and acquires projection data for the first slice. Since the value of projection data corresponds to the receive strength of an MR signal, the RF level determination function 131b determines the transmit strength of an RF signal (for example, 54 dB in FIG. 4) for which the receive strength of an MR signal becomes a maximum value as the initial RF level. The transmit strength of an RF signal may be changed consecutively or step by step.

If the initial RF level is not determined, the RF level determination function 131b may calculate power of the first RF magnetic field required for excitation at a first flip angle in the first target slice in step S201.

(Step S202)

The processing circuitry 131, via the cross section specification function 131c, specifies a cross section of the target organ by executing locator imaging. Specifically, the processing circuitry 131, via the cross section specification function 131c, specifies at least a second slice and a third slice.

The second slice and the third slice will be described with reference to FIGS. 5 and 6. The second slice is, for example, a slice for a cardiac axis cross section 502 that includes a cardiac axis 501 of the heart 301. If the second slice is identified, the magnetic resonance imaging apparatus 100 may reconstruct an image 601 of the cardiac axis cross section 502. The image 601 includes a cardiac muscle region 602. The third slice is, for example, a slice for a cross section of a slice position 603 crossing the cardiac axis 501.

If the operator selects the second slice and the third slice via the interface 125, this step can be omitted.

(Step S203)

The processing circuitry 131, via the time phase information acquisition function 131d, acquires information on the time phase related to a timing of imaging the third slice from an imaging plan. For example, if the imaging plan is "cine imaging of the heart", it is desirable to generate two $B_1$ maps of "contraction time" and "expansion time". Accordingly, the processing circuitry 131, via the time phase information acquisition function 131d, acquires information for two time phases of the "contraction time" and the "expansion time". The processing circuitry 131, via the time phase information acquisition function 131d, may acquire a cardiac time phase which is a timing of acquiring information on inhomogeneity of the transmission RF magnetic field.

(Step S204)

The processing circuitry 131, via the $B_1$ map generation function 131e, generates a $B_1$ map related to the second RF pulse, based on a second MR signal received along with transmission of the second RF pulse having the initial RF level to the second slice.

Figures 7, 8:
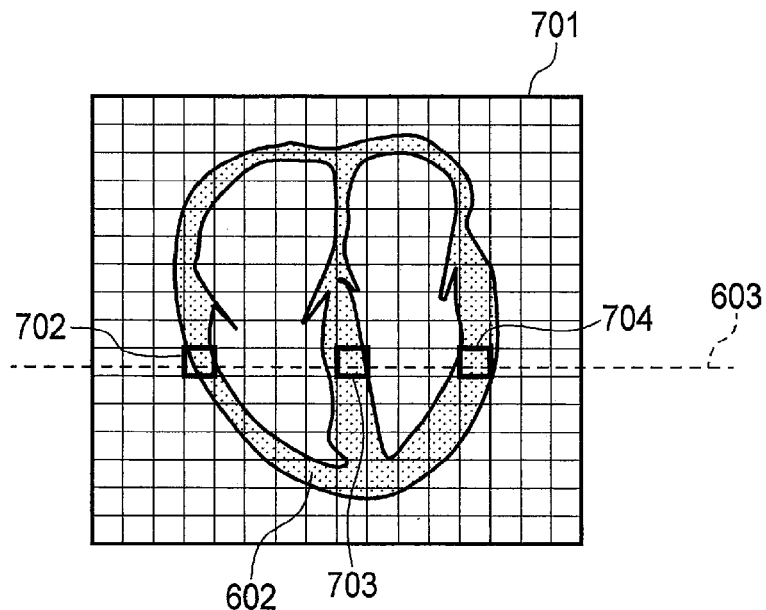
FIG. 7 illustrates a $B_1$ map of the cross section including the cardiac axis of the heart, according to the embodiment.
FIG. 8 is a table in which a pixel value of $B_1$ map is associated with an adjustment value of an RF level, according to the embodiment.

The $B_1$ map will be described with reference to FIGS. 6 and 7. The processing circuitry 131, via the $B_1$ map generation function 131e, generates a $B_1$ map 701 corresponding to the image 601. The cardiac muscle region 602 that may be displayed on the image 601 is placed at the same position in the $B_1$ map 701. Namely, the slice position 603 in the $B_1$ map 701 includes a pixel 702, a pixel 703, and a pixel 704 corresponding to the cardiac muscle region 602.

If a $B_1$ map is not generated, the $B_1$ map generation function 131e may acquire information on inhomogeneity of the transmission RF magnetic field for a cross section crossing the first target slice in step S204.

(Step S205)

The processing circuitry 131, via the adjustment value determination function 131f, determines an adjustment value of an RF level for the third slice, based on a plurality of pixel values included in the tissue region of the target organ in the $B_1$ map. Specifically, the processing circuitry 131, via the adjustment value determination function 131f, determines an adjustment value of the RF level for a short axis cross section of the heart based on an average value of the pixel values of the pixel 702, the pixel 703, and the pixel 704 included in the partial region corresponding to the slice position 603 among the cardiac muscle region 602 in the $B_1$ map 701. The adjustment value of RF level is determined by using a look up table as shown in FIG. 8. For example, when the average value of the pixel values of the pixel 702, the pixel 703, and the pixel 704 is 75, the adjustment value of the RF level is "R_2".

(Step S206)

The processing circuitry 131, via the adjustment function 131g, adjusts the initial RF level by using the adjustment value determined in step S205. Specifically, the processing circuitry 131, via the adjustment function 131g, adjusts the initial RF level by using, for example, the adjustment value "R_2".

If a $B_1$ map is not generated, the processing circuitry 131, via the adjustment value determination function 131f and the adjustment function 131g, calculates power of the second RF magnetic field required for excitation at a second flip angle in a second target slice, different from the first target slice, for a cross section crossing the first target slice by using information on inhomogeneity of the transmission RF magnetic field and the first RF magnetic field power in step S205 and step S206.

(Step S207)

Figure 9:
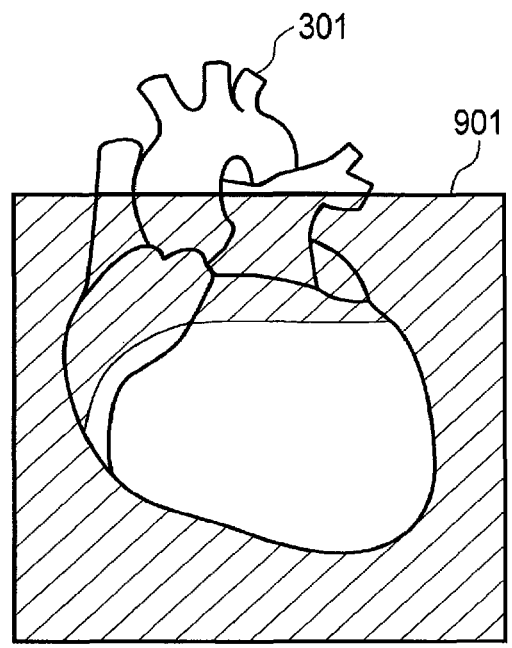
FIG. 9 illustrates a cross section position of the left ventricle in a short axis direction, according to the embodiment.
Figure 10:
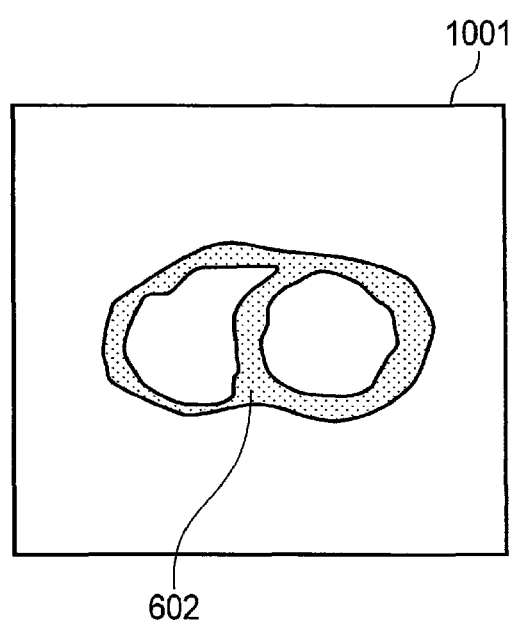
FIG. 10 is a cross-sectional image of the left ventricle in the short axis direction, according to the embodiment.

The imaging control circuitry 121 images the third slice by using the third RF pulse having an RF level adjusted in step S206. Specifically, the imaging control circuitry 121 images the third slice that includes a short axis cross section 901 shown in FIG. 9, by using the third RF pulse. Via imaging the third slice, the magnetic resonance imaging apparatus 100 reconstructs an image 1001 shown in FIG. 10.

If the third RF pulse is not used, the imaging control circuitry 121 performs an imaging scan based on power of the second RF magnetic field in step S207.

As described above, according to an embodiment, the magnetic resonance imaging apparatus 100 determines an RF level indicating a level of power supplied to an RF coil, based on a plurality of first MR signals corresponding to a plurality of first RF pulses transmitted to the first slice for a target organ, and generates a $B_1$ map representing the strength distribution of the magnetic field related to the second RF pulse, based on the second MR signal received in accordance with transmission of the second RF pulse having the determined RF level to the second slice for the target organ. Thereafter, the magnetic resonance imaging apparatus 100 determines an adjustment value of the determined RF level related to the third slice set relative to the target organ based on the plurality of pixel values included in the tissue region among the target organ in the $B_1$ map, adjusts the determined RF level by using the adjustment value, and can image the third slice by using the third RF pulse having the adjusted RF level. Via the above processing, the magnetic resonance imaging apparatus 100 can set an RF level suitable for imaging on the target organ.

The magnetic resonance imaging apparatus 100 can determine an adjustment value based on an average value of pixel values included in a partial region corresponding to the third slice in the $B_1$ map within the tissue region. Via this processing, the magnetic resonance imaging apparatus 100 can set an RF level suitable for imaging on the target organ.

The magnetic resonance imaging apparatus 100 can set the heart as the target organ, set the second slice to include the cardiac axis of the heart, and set a cardiac muscle region as the tissue region. Via this processing, the magnetic resonance imaging apparatus 100 can set an RF level suitable for imaging on the cardiac muscle of the heart.

The magnetic resonance imaging apparatus 100 can generate a $B_1$ map corresponding to a time phase of at least one of the contraction time and the expansion time of the cardiac cycle of heart. Via this processing, the magnetic resonance imaging apparatus 100 can generate a $B_1$ map corresponding to the cardiac time phase, thereby setting an RF level suitable for $B_1$ map imbalance according to the shape change of the heart.

The magnetic resonance imaging apparatus 100 can generate a $B_1$ map corresponding to a time phase of at least one of the exhalation phase and the inhalation phase of breathing of the subject. Via this processing, the magnetic resonance imaging apparatus 100 can generate a $B_1$ map corresponding to breathing of the subject, thereby setting an RF level suitable for $B_1$ map imbalance according to the shape change of the target organ.

The magnetic resonance imaging apparatus 100 acquires information on a time phase related to a timing of imaging the third slice from the imaging plan that indicates the procedure of imaging, and can generate a $B_1$ map corresponding to the acquired time phase. Via this processing, the magnetic resonance imaging apparatus 100 can use an RF level in accordance with the time phase change, thereby setting an RF level suitable for consecutive imaging such as cine imaging.

The magnetic resonance imaging apparatus 100 can acquire a second MR signal by using the method for suppressing an MR signal from a blood vessel in the target organ. Via this processing, the magnetic resonance imaging apparatus 100 can suppress a signal from the blood region on the $B_1$ map, thereby detecting a signal from the tissue region of the target region with high accuracy.

Thus, the magnetic resonance imaging apparatus 100 can set an RF level suitable for imaging on the target organ. Specifically, the magnetic resonance imaging apparatus 100 can perform optimization at around the cardiac apex of the heart, which is difficult for an RF signal to reach, by setting a suitable RF level, and accordingly, can improve an image quality of cine imaging that is frequently used in cardiac imaging.

In addition, according to an embodiment, the magnetic resonance imaging apparatus 100 calculates power of a first RF magnetic field required for excitation at a first flip angle in a first target slice, acquires information relative to inhomogeneity of a transmission RF magnetic field related to a cross section crossing the first target slice, and calculates power of a second RF magnetic field required for excitation at the second flip angle in a second target slice different from the first target slice for the cross section crossing the first target slice by using information on inhomogeneity of the transmission RF magnetic field and the first RF magnetic field power.

The magnetic resonance imaging apparatus 100 can use a $B_1$ map representing spatial inhomogeneity of the transmission RF magnetic field relative to the first flip angle, as the information on inhomogeneity of the transmission RF magnetic field.

The magnetic resonance imaging apparatus 100 can set the cross section crossing the first target slice to include a long axis of a heart of a subject that is an imaging target.

The magnetic resonance imaging apparatus 100 further performs an imaging scan based on the power of the second RF magnetic field, acquires a cardiac time phase at a timing of acquiring information on inhomogeneity of the transmission RF magnetic field, and can perform the imaging scan in the cardiac time phase.

According to at least an embodiment described above, the power of an RF magnetic field suitable for imaging on a target organ can be calculated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A magnetic resonance imaging apparatus, comprising: processing circuitry configured to:
    calculate a first RF level of a first RF signal required for excitation at a first flip angle in a first target slice of a region of a subject which includes a target organ that is an imaging target;
    acquire information on inhomogeneity of a transmission RF magnetic field by transmission of a second RF signal having the first RF level for a cross section of the target organ which crosses the first target slice; and
    calculate a second RF level of the second RF signal required for excitation at a second flip angle in a second target slice of the target organ that is different from the first target slice for the cross section by using the information on the inhomogeneity for the cross section and the first RF level.

2. The magnetic resonance imaging apparatus according to claim 1, wherein:
the information is a $B_1$ map representing spatial inhomogeneity of the transmission RF magnetic field relative to the first flip angle.

3. The magnetic resonance imaging apparatus according to claim 1, wherein the cross section includes a long axis of a heart of the subject which is the target organ.

4. The magnetic resonance imaging apparatus according to claim 1, further comprising:
an imaging unit configured to perform an imaging scan using the second RF signal having the second RF level,
wherein the processing circuitry is further configured to:
acquire information of a time phase in which the target organ is at a timing of acquiring the information on the inhomogeneity of the transmission RF magnetic field or imaging scan of the second target slice of the target organ is performed; and
acquire the information on the inhomogeneity of the transmission RF magnetic field according to the information of the time phase.

5. The magnetic resonance imaging apparatus according to claim 4, wherein
the information on a time phase relates to a timing of imaging the second slice from an imaging plan that indicates a procedure of imaging.

6. The magnetic resonance imaging apparatus according to claim 1, wherein calculating the first RF level comprises determining the first RF level based on a plurality of first MR signals corresponding to a plurality of first RF pulses of the first RF signal transmitted to the first slice for a target organ, wherein the first RF level indicates a level of power supplied to an RF coil, the magnetic resonance imaging apparatus further comprising
an imaging unit, and
wherein the processing circuitry is further configured to:
generate a $B_1$ map representing a strength distribution of a magnetic field related to the second RF signal, based on a second MR signal received in accordance with transmission of the second RF signal having the first RF level to the cross section of the target organ;
determine an adjustment value to adjust the first RF level for the second target slice of the target organ based on a plurality of pixel values included in a tissue region among the target organ in the $B_1$ map; and
adjust the first RF level by using the adjustment value to calculate the second RF level of the second RF signal
wherein the imaging unit is configured to image the second target slice by using the second RF signal having the second RF level.

7. The magnetic resonance imaging apparatus according to claim 6, wherein the processing circuitry is further configured to determine the adjustment value based on an average value of pixel values included in a partial region of the tissue region corresponding to the second target slice in the $B_1$ map.

8. The magnetic resonance imaging apparatus according to claim 6, wherein:
the target organ is a heart;
the cross section of the target organ includes a cardiac axis of the heart; and
the tissue region is a cardiac muscle region of the heart.

9. The magnetic resonance imaging apparatus according to claim 6, wherein the processing circuitry is further configured to acquire the second MR signal by using a method for suppressing an MR signal from a blood vessel in the target organ.

10. The magnetic resonance imaging apparatus according to claim 1, wherein:
the target organ is a heart, and
the information on the inhomogeneity of the transmission RF magnetic field corresponds to a time phase of at least one of a contraction time and an expansion time of a cardiac cycle of the heart.

11. The magnetic resonance imaging apparatus according to claim 1, wherein the information on the inhomogeneity of the transmission RF magnetic field corresponds to a time phase of at least one of an exhalation phase and an inhalation phase of breathing of the subject.

12. The magnetic resonance imaging apparatus according to claim 1, wherein the cross section of the target organ which crosses the first target slice is a representative cross section of the target organ.

* * * * *